(12) United States Patent
Oomura et al.

(10) Patent No.: US 8,324,283 B2
(45) Date of Patent: Dec. 4, 2012

(54) SOLID PHARMACEUTICAL COMPOSITIONS COMPRISING A S1P RECEPTOR AGONIST AND A SUGAR ALCOHOL

(75) Inventors: Tomoyuki Oomura, Oita (JP); Madhusudhan Pudipeddi, Edison, NJ (US); Colleen Ruegger, Morris Plains, NJ (US); Alan E Royce, Saylorsburg, PA (US); Masaki Sasaki, Oita (JP); Tokuhiro Tamura, Fukuoka (JP)

(73) Assignees: Novartis AG, Basel (CH); Mitsubishi Pharma Corporation, Osaka (JP)

( * ) Notice: Subject to any disclaimer, the term of this patent is extended or adjusted under 35 U.S.C. 154(b) by 722 days.

(21) Appl. No.: 12/189,323

(22) Filed: Aug. 11, 2008

(65) Prior Publication Data

US 2008/0311188 A1 Dec. 18, 2008

Related U.S. Application Data

(62) Division of application No. 10/552,005, filed as application No. PCT/EP2004/003656 on Apr. 6, 2004, now abandoned.

(60) Provisional application No. 60/461,215, filed on Apr. 8, 2003.

(51) Int. Cl.
*A01N 33/02* (2006.01)
*A61K 31/135* (2006.01)

(52) U.S. Cl. ...................................... 514/649

(58) Field of Classification Search ................. 514/649
See application file for complete search history.

(56) References Cited

U.S. PATENT DOCUMENTS

| | | | |
|---|---|---|---|
| 4,110,322 A | 8/1978 | Greven et al. | 260/112.5 R |
| 5,112,616 A | 5/1992 | McCarty | |
| 6,277,888 B1 * | 8/2001 | Sakai et al. | 514/653 |
| 6,476,004 B1 | 11/2002 | Sakai et al. | |
| 7,151,093 B2 | 12/2006 | Kishikawa et al. | 514/114 |
| 2002/0155512 A1 | 10/2002 | Liao et al. | |

FOREIGN PATENT DOCUMENTS

| | | |
|---|---|---|
| EP | 0142078 | 5/1985 |
| EP | 0 812 588 | 12/1997 |
| EP | 0 627 406 | 10/1998 |
| EP | 0 990 440 | 4/2000 |
| EP | 1 002 792 | 5/2000 |
| EP | 1 050 301 | 11/2000 |
| EP | 1 195 165 | 4/2002 |
| EP | 1 300 405 | 4/2003 |
| EP | 1424078 A1 | 6/2004 |
| EP | 1 201 236 | 9/2006 |
| JP | 4-202131 | 7/1992 |
| JP | 11276191 | 10/1999 |
| JP | 2002 2412 72 | 8/2002 |
| WO | 98/03162 | 1/1998 |
| WO | 02/18395 | 3/2002 |
| WO | WO 02/085290 | 10/2002 |
| WO | WO 03/061567 | 7/2003 |
| WO | WO 03/062392 | 7/2003 |

OTHER PUBLICATIONS

Kiuchi et al., "Synthesis and immunosuppressive activity of 2-substituted 2-aminopropane-1,3-diols and 2-aminoethanois", Journal of Med. Chem., 2000, vol. 43, pp. 2946-2961.
Mandala et al., "Alteration of lymphocyte trafficking by sphingosine-1-phosphate receptor agonists", Science, 2002, vol. 296, pp. 346-349.
Remington's pharmaceutical sciences (Ed. Alfonso R. Gennaro, 1990, 18th edn.).
Parteck M200 MSDS (accessed Jul. 1, 2010 from http://setonresourcecenter.com/msdshazcom/htdocs/MSDS/E/EMD/Docs/wcd00028/wcd02803.pdf#search+"granular").
Turk (Micronization of Pharmaceutical substances by the rapid expansion of Supercritical Solutions (RESS): a promising method to improve bioavailability of poorly soluble pharmaceutical agents. Journal of Supercritical Fluids, vol. 22, pp. 75-84, 2002).
Honig et al., "FTY stimulates multidrug transporter and cysteinyl leukotriene-dependent T cell chemotaxis to lymph nodes", The Journal of Clinical Investigations, 2003, vol. 111, No. 5, p. 627-637.
Yoshiki, Yanagawa et al., "FTY720, a Novel Immunosuppressant, Induces Sequestration of Circulating Mature Lymphocytes by Acceleration of Lymphocyte Homing in Rats. II. FTY720 Prolongs Skin Allograft Survival by Decreasing T Cell Infiltration into Grafts But Not Cytokine Production in Vivo", The Journal of Immunology, vol. 160, pp. 5493-5499, (1998).
Masayuki, Fujino et al., "Amelioration of Experimental Autoimmune Encephalomyelitis in Lewis Rats by FTY720 Treatment", The Journal of Pharmacology and Experimental Therapeutics, vol. 305, No. 1, pp. 70-77, (2003).
Volker, Brinkmann et al., "The Immune Modulator FTY720 Targets Sphingosine 1-Phosphate Receptors", The Journal of Biological Chemistry, vol. 277, No. 24, pp. 21453-21457, (2002).
English translation of Chemical Engineer, 2000, 2, No. 77, Application and Manufacture of Mannitol.
Remington's Pharmaceutical Sciences, "Solid Oral Forms", vol. 2, chapter 92, 19 Ed. 1998.

* cited by examiner

*Primary Examiner* — Benjamin Packard
(74) *Attorney, Agent, or Firm* — Karen DeBenedictis

(57) ABSTRACT

A solid pharmaceutical composition suitable for oral administration, comprising:
(a) a S1P receptor agonist; and
(b) a sugar alcohol.

32 Claims, No Drawings

SOLID PHARMACEUTICAL COMPOSITIONS COMPRISING A S1P RECEPTOR AGONIST AND A SUGAR ALCOHOL

This is a divisional of application Ser. No. 10/552,005 filed on Nov. 14, 2005, which is National Stage of International Application No. PCT/EP2004/003656 filed on Apr. 6, 2004, which claims benefit of provisional Application 60/461,215 filed on Apr. 8, 2003, the entire disclosures of which are hereby incorporated by reference.

The present invention relates to pharmaceutical compositions comprising a sphingosine-1 phosphate receptor agonist. Sphingosine-1 phosphate (hereinafter "S1P") is a natural serum lipid. Presently there are 8 known S1P receptors, namely S1P1 to S1P8. S1P receptor agonists have accelerating lymphocyte homing properties.

S1P receptor agonists are immunomodulating compounds which elicit a lymphopenia resulting from a re-distribution, preferably reversible, of lymphocytes from circulation to secondary lymphatic tissue, evoking a generalized immunosuppression. Naive cells are sequestered, CD4 and CD8 T-cells and B-cells from the blood are stimulated to migrate into lymph nodes (LN) and Peyer's patches (PP), and thus infiltration of cells into transplanted organs is inhibited.

The various known S1P receptor agonists show structural similarities, which result in related problems in providing a suitable formulation. In particular, there is a need for an S1P receptor agonist containing formulation which is well-adapted for oral administration in a solid form, e.g. as a tablet or capsule.

Accordingly, the present invention provides a solid pharmaceutical composition suitable for oral administration, comprising a S1P receptor agonist and a sugar alcohol.

It has surprisingly been found that solid compositions comprising a sugar alcohol provide formulations which are particularly well suited to the oral administration of S1P receptor agonists. The compositions provide a convenient means of systemic administration of S1P receptor agonists, do not suffer from the disadvantages of liquid formulations for injection or oral use, and have good physicochemical and storage properties. In particular, the compositions of the present invention may show a high level of uniformity in the distribution of the S1P receptor agonist throughout the composition, as well as high stability. The compositions of the invention may be manufactured on high speed automated equipment, and thus do not require hand encapsulation.

S1P receptor agonists are typically sphingosine analogues, such as 2-substituted 2-amino-propane-1,3-diol or 2-aminopropanol derivatives. Examples of appropriate S1P receptor agonists are, for example:
  Compounds as disclosed in EP627406A1, e.g. a compound of formula I

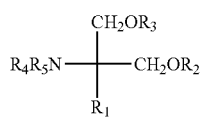

wherein $R_1$ is a straight- or branched ($C_{12-22}$)carbon chain
  which may have in the chain a bond or a hetero atom selected from a double bond, a triple bond, O, S, $NR_6$, wherein $R_6$ is H, alkyl, aralkyl, acyl or alkoxycarbonyl, and carbonyl, and/or
  which may have as a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxyimino, hydroxy or carboxy; or
$R_1$ is
  a phenylalkyl wherein alkyl is a straight- or branched ($C_{6-20}$)carbon chain; or
  a phenylalkyl wherein alkyl is a straight- or branched ($C_{1-30}$)carbon chain wherein said phenylalkyl is substituted by
  a straight- or branched ($C_{6-20}$)carbon chain optionally substituted by halogen,
  a straight- or branched ($C_{6-20}$)alkoxy chain optionally substituted by halogen,
  a straight- or branched ($C_{6-20}$)alkenyloxy,
  phenylalkoxy, halophenylalkoxy, phenylalkoxyalkyl, phenoxyalkoxy or phenoxyalkyl,
  cycloalkylalkyl substituted by $C_{6-20}$alkyl,
  heteroarylalkyl substituted by $C_{6-20}$alkyl,
  heterocyclic $C_{6-20}$alkyl or
  heterocyclic alkyl substituted by $C_{2-20}$alkyl,
and wherein
the alkyl moiety may have
  in the carbon chain, a bond or a heteroatom selected from a double bond, a triple bond, O, S, sulfinyl, sulfonyl, or $NR_6$, wherein $R_6$ is as defined above, and
  as a substituent alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy, and
each of $R_2$, $R_3$, $R_4$ and $R_5$, independently, is H, $C_{1-4}$ alkyl or acyl
or a pharmaceutically acceptable salt thereof;
  Compounds as disclosed in EP 1002792A1, e.g. a compound of formula II

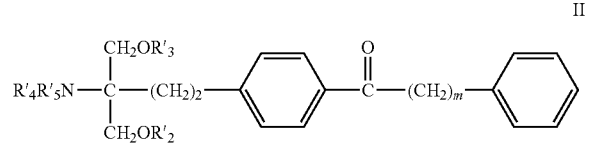

wherein m is 1 to 9 and each of $R'_2$, $R'_3$, $R'_4$ and $R'_5$, independently, is H, alkyl or acyl,
or a pharmaceutically acceptable salt thereof;
  Compounds as disclosed in EP0778263 A1, e.g. a compound of formula III

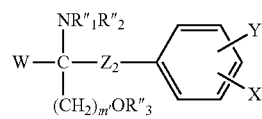

wherein W is H; $C_{1-6}$alkyl, $C_{2-6}$alkenyl or $C_{2-6}$alkynyl; unsubstituted or by OH substituted phenyl; $R''_4O(CH_2)_n$; or $C_{1-6}$alkyl substituted by 1 to 3 substituents selected from the group consisting of halogen, $C_{3-8}$cycloalkyl, phenyl and phenyl substituted by OH;
X is H or unsubstituted or substituted straight chain alkyl having a number p of carbon atoms or unsubstituted or substituted straight chain alkoxy having a number (p-1) of carbon atoms, e.g. substituted by 1 to 3 substitutents selected from the group consisting of $C_{1-6}$ alkyl, OH, $C_{1-6}$alkoxy, acyloxy, amino, $C_{1-6}$alkylamino, acylamino, oxo, halo$C_{1-6}$alkyl, halogen, unsubstituted phenyl and phenyl substituted by 1 to 3 substituents selected from the group consisting of $C_{1-6}$alkyl, OH, $C_{1-6}$alkoxy, acyl, acyloxy, amino, $C_{1-4}$alkylamino, acylamino, halo$C_{1-6}$alkyl and halogen; Y is H, $C_{1-6}$alkyl, OH, $C_{1-6}$alkoxy, acyl, acyloxy, amino, $C_{1-6}$alkylamino, acylamino, halo$C_{1-6}$alkyl or halogen, $Z_2$ is a single bond or a straight chain alkylene having a number or carbon atoms of q, each of p and q, independently, is an integer of 1 to 20, with the proviso of $6 \leq p+q \leq 23$, m' is 1, 2 or 3, n is 2 or 3, each of $R''_1$, $R''_2$, $R''_3$ and $R''_4$, independently, is H, $C_{1-4}$alkyl or acyl, or a pharmaceutically acceptable salt thereof, Compounds as disclosed in WO02/18395, e.g. a compound of formula IVa or IVb

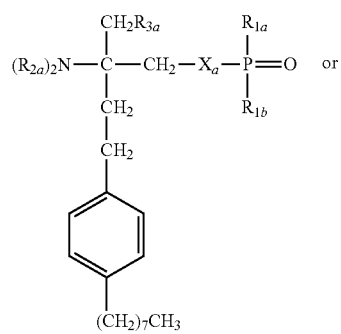

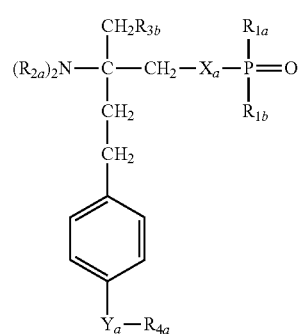

wherein $X_a$ is O, S, $NR_{1s}$ or a group —$(CH_2)_{na}$—, which group is unsubstituted or substituted by 1 to 4 halogen; $n_a$ is 1 or 2, $R_{1s}$ is H or $(C_{1-4})$alkyl, which alkyl is unsubstituted or substituted by halogen; $R_{1a}$ is H, OH, $(C_{1-4})$alkyl or $O(C_{1-4})$alkyl wherein alkyl is unsubstituted or substituted by 1 to 3 halogen; $R_{1b}$ is H, OH or $(C_{1-4})$alkyl, wherein alkyl is unsubstituted or substituted by halogen; each $R_{2a}$ is independently selected from H or $(C_{1-4})$alkyl, which alkyl is unsubstituted or substituted by halogen; $R_{3a}$ is H, OH, halogen or $O(C_{1-4})$alkyl wherein alkyl is unsubstituted or substituted by halogen; and $R_{3b}$ is H, OH, halogen, $(C_{1-4})$alkyl wherein alkyl is unsubstituted or substituted by hydroxy, or $O(C_{1-4})$alkyl wherein alkyl is unsubstituted or substituted by halogen; $Y_a$ is —$CH_2$—, —$C(O)$—, —$CH(OH)$—, —$C(=NOH)$—, O or S, and $R_{4a}$ is $(C_{4-14})$alkyl or $(C_{4-14})$alkenyl;

or a pharmaceutically acceptable salt or hydrate thereof;

Compounds as disclosed in WO 02/076995, e.g. a compound of formula V

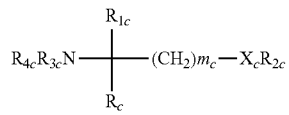

wherein $m_c$ is 1, 2 or 3;

$X_c$ is O or a direct bond;

$R_{1c}$ is H; $CO_{1-6}$ alkyl optionally substituted by OH, acyl, halogen, $C_{3-10}$cycloalkyl, phenyl or hydroxy-phenylene; $C_{2-6}$alkenyl; $C_{2-6}$alkynyl; or phenyl optionally substituted by OH;

$R_{2c}$ is

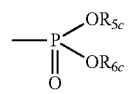

wherein $R_{5c}$ is H or $C_{1-4}$alkyl optionally substituted by 1, 2 or 3 halogen atoms, and $R_{6c}$ is H or $C_{1-4}$alkyl optionally substituted by halogen;

each of $R_{3c}$ and $R_{4c}$, independently, is H, $C_{1-4}$alkyl optionally substituted by halogen, or acyl, and $R_c$ is $C_{13-20}$alkyl which may optionally have in the chain an oxygen atom and which may optionally be substituted by nitro, halogen, amino, hydroxy or carboxy; or a residue of formula (a)

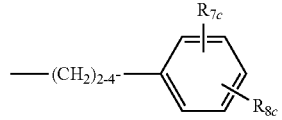

wherein $R_{7c}$ is H, $C_{1-4}$alkyl or $C_{1-4}$alkoxy, and r is substituted $C_{1-20}$alkanoyl, phenyl$C_{1-14}$alkyl wherein the $C_{1-14}$alkyl is optionally substituted by halogen or OH, cycloalkyl$C_{1-14}$alkoxy or phenyl$C_{1-14}$alkoxy wherein the cycloalkyl or phenyl ring is optionally substituted by halogen, $C_{1-4}$alkyl and/or $CO_{1-4}$alkoxy, phenyl$C_{1-14}$alkoxy-$C_{1-14}$alkyl, phenoxy$C_{1-14}$alkoxy or phenoxy$C_{1-14}$alkyl, $R_c$ being also a residue of formula (a) wherein $R_{8c}$ is $C_{1-14}$alkoxy when $R_{1c}$ is $C_{1-4}$alkyl, $C_{2-6}$alkenyl or $C_{2-6}$alkynyl, or a compound of formula VI

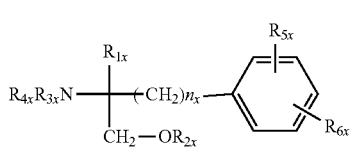

wherein
$n_x$ is 2, 3 or 4
$R_{1x}$ is H; $C_{1-6}$alkyl optionally substituted by OH, acyl, halogen, cycloalkyl, phenyl or hydroxy-phenylene; $C_{2-6}$alkenyl; $C_{2-6}$alkynyl; or phenyl optionally substituted by OH;
$R_{2x}$ is H, $C_{1-4}$ alkyl or acyl
each of $R_{3x}$ and $R_{4x}$, independently is H, $C_{1-4}$alkyl optionally substituted by halogen or acyl,
$R_{5x}$ is H, $C_{1-4}$alkyl or $C_{1-4}$alkoxy, and
$R_{6x}$ is $C_{1-20}$alkanoyl substituted by cycloalkyl; cyloalkyl$C_{1-14}$alkoxy wherein the cycloalkyl ring is optionally substituted by halogen, $C_{1-4}$alkyl and/or $C_{1-4}$alkoxy; phenyl$C_{1-14}$alkoxy wherein the phenyl ring is optionally substituted by halogen, $C_{1-14}$alkyl and/or $C_{1-14}$alkoxy,
$R_{6x}$ being also $C_{4-14}$alkoxy when $R_{1x}$ is $C_{2-4}$alkyl substituted by OH, or pentyloxy or hexyloxy when $R_{1x}$ is $C_{4-14}$-alkyl, provided that $R_{6x}$ is other than phenyl-butylenoxy when either $R_{5x}$ is H or $R_{1x}$ is methyl,
or a pharmaceutically acceptable salt thereof;

Compounds as disclosed in WO02/06268A1, e.g. a compound of formula VII

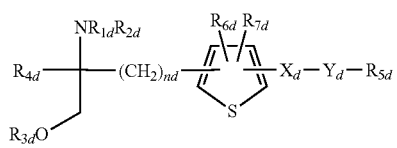

wherein each of $R_{1d}$ and $R_{2d}$, independently, is H or an amino-protecting group;
$R_{3d}$ is hydrogen, a hydroxy-protecting group or a residue of formula

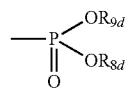

$R_{4d}$ is lower alkyl;
$n_d$ is an integer of 1 to 6;
$X_d$ is ethylene, vinylene, ethynylene, a group having a formula -D-CH$_2$— (wherein D is carbonyl, —CH(OH)—, O, S or N), aryl or aryl substituted by up to three substitutents selected from group a as defined hereinafter;
$Y_d$ is single bond, $C_{1-10}$alkylene, $C_{1-10}$alkylene which is substituted by up to three substitutents selected from groups a and b, $C_{1-10}$alkylene having O or S in the middle or end of the carbon chain, or $C_{1-10}$alkylene having O or S in the middle or end of the carbon chain which is substituted by up to three substituents selected from groups a and b;
$R_{5d}$ is hydrogen, cycloalkyl, aryl, heterocycle, cycloalkyl substituted by up to three substituents selected from groups a and b, aryl substituted by up to three substituents selected from groups a and b, or heterocycle substituted by up to three substituents selected from groups a and b;
each of $R_{6d}$ and $R_{7d}$, independently, is H or a substituent selected from group a;
each of $R_{8d}$ and $R_{9d}$, independently, is H or $C_{1-4}$alkyl optionally substituted by halogen;
<group a> is halogen, lower alkyl, halogeno lower alkyl, lower alkoxy, lower alkylthio, carboxyl, lower alkoxycarbonyl, hydroxy, lower aliphatic acyl, amino, mono-lower alkylamino, di-lower alkylamino, lower aliphatic acylamino, cyano or nitro; and <group b> is cycloalkyl, aryl, heterocycle, each being optionally substituted by up to three substituents selected from group a;
with the proviso that when $R_{5d}$ is hydrogen, $Y_d$ is a group exclusive of single bond and linear $C_{1-10}$ alkylene, or a pharmacologically acceptable salt or ester thereof;

Compounds as disclosed in JP-14316985 (JP2002316985), e.g. a compound of formula VII:

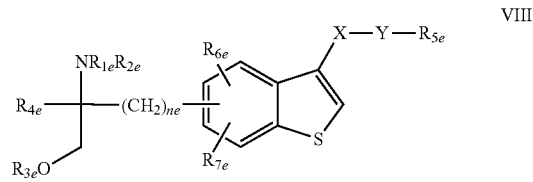

wherein $R_{1e}$, $R_{2e}$, $R_{3e}$, $R_{4e}$, $R_{5e}$, $R_{6e}$, $R_{7e}$, $n_e$, $X_e$ and $Y_e$ are as disclosed in JP-14316985;
or a pharmacologically acceptable salt or ester thereof;

Compounds as disclosed in WO 03/29184 and WO 03/29206, e.g. compounds of formula IX

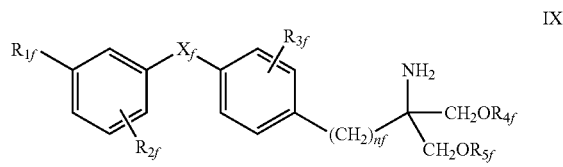

wherein $X_f$ is O or S, and $R_{1f}$, $R_{2f}$, $R_{3f}$ and $n_f$ are as disclosed in WO 03/29184 and 03/29205,
each of $R_{4f}$ and $R_{5f}$, independently is H or a residue of formula

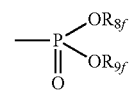

wherein each of $R_{8f}$ and $R_{9f}$, independently, is H or $C_{1-4}$alkyl optionally substituted by halogen; e.g. 2-amino-2-[4-(3-benzyloxyphenoxy)-2-chlorophenyl]propyl-1,3-propane-diol or 2-amino-2-[4-(benzyloxyphenylthio)-2-chlorophenyl]propyl-1,3-propane-diol, or a pharmacological salt thereof.

Compounds as disclosed in WO03062252A1, e.g. a compound of formula X

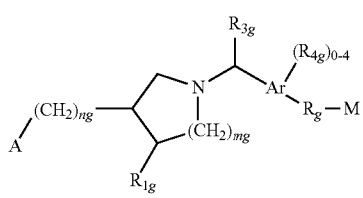

wherein
Ar is phenyl or naphthyl; each of mg and ng independently is 0 or 1; A is selected from COOH, PO3H2, PO2H, SO3H, PO(C1-3alkyl)OH and 1H-tetrazol-5-yl; each of R1g and R2g independently is H, halogen, OH, COOH or C1-4alkyl optionally substituted by halogen; R3g is H or C1-4alkyl optionally substituted by halogen or OH; each R4g independently is halogen, or optionally halogen substituted C1-4alkyl or C1-3alkoxy; and each of R9 and M has one of the significances as indicated for B and C, respectively, in WO03/062252A1;

Compounds as disclosed in WO 03/062248A2, e.g. a compound of formula XI

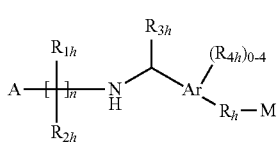

wherein Ar is phenyl or naphthyl; n is 2, 3 or 4; A is COOH, 1H-tetrazol-5-yl, PO3H2, PO2H2, —SO3H or PO(R5h)OH wherein R5h is selected from C1-4alkyl, hydroxyC1-4alkyl, phenyl, —CO—C1-3alkoxy and —CH(OH)-phenyl wherein said phenyl or phenyl moiety is optionally substituted; each of R1h and R2h independently is H, halogen, OH, COOH, or optionally halogeno substituted C1-6alkyl or phenyl; R3h is H or C1-4alkyl optionally substituted by halogen and/OH; each R4h independently is halogeno, OH, COOH, C1-4alkyl, S(O)0, 1 or 2C1-3alkyl, C1-3alkoxy, C3-6cycloalkoxy, aryl or aralkoxy, wherein the alkyl portions may optionally be substituted by 1-3 halogens; and each of Rg and M has one of the significances as indicated for B and C, respectively, in WO03/062248A2.

According to a further embodiment of the invention, a S1P receptor agonist for use in a combination of the invention may also be a selective S1P1 receptor, e.g. a compound which possesses a selectivity for the S1P1 receptor over the S1P3 receptor of at least 20 fold, e.g. 100, 500, 1000 or 2000 fold, as measured by the ratio of EC50 for the S1P1 receptor to the EC50 for the S1P3 receptor as evaluated in a 35S-GTPγS binding assay, said compound having an EC50 for binding to the S1P1 receptor of 100 nM or less as evaluated by the 35S-GTPγS binding assay. Representative S1P1 receptor agonists are e.g. the compounds listed in WO 03/061567, the contents of which being incorporated herein by reference, for instance a compound of formula

XII

XIII

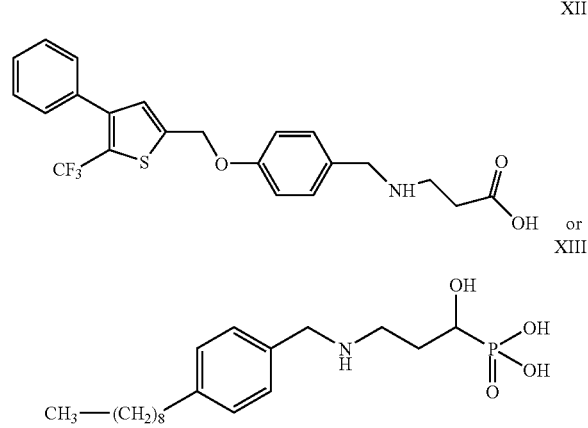

In each case where citations of patent applications are given, the subject matter relating to the compounds is hereby incorporated into the present application by reference.

Acyl may be a residue $R_y$—CO— wherein $R_y$ is $C_{1-4}$alkyl, $C_{3-6}$cycloalkyl, phenyl or phenyl-$C_{1-4}$alkyl. Unless otherwise stated, alkyl, alkoxy, alkenyl or alkynyl may be straight or branched.

When in the compounds of formula I the carbon chain as $R_1$ is substituted, it is preferably substituted by halogen, nitro, amino, hydroxy or carboxy. When the carbon chain is interrupted by an optionally substituted phenylene, the carbon chain is preferably unsubstituted. When the phenylene moiety is substituted, it is preferably substituted by halogen, nitro, amino, methoxy, hydroxy or carboxy.

Preferred compounds of formula I are those wherein $R_1$ is $C_{13-20}$alkyl, optionally substituted by nitro, halogen, amino, hydroxy or carboxy, and, more preferably those wherein $R_1$ is phenylalkyl substituted by $C_{6-14}$-alkyl chain optionally substituted by halogen and the alkyl moiety is a $C_{1-6}$alkyl optionally substituted by hydroxy. More preferably, $R_1$ is phenyl-$C_{1-6}$alkyl substituted on the phenyl by a straight or branched, preferably straight, $C_{6-14}$alkyl chain. The $C_{6-14}$alkyl chain may be in ortho, meta or para, preferably in para.

Preferably each of $R_2$ to $R_5$ is H.

A preferred compound of formula I is 2-amino-2-tetradecyl-1,3-propanediol. A particularly preferred S1P receptor agonist of formula I is FTY720, i.e. 2-amino-2-[2-(4-octylphenyl) ethyl]propane-1,3-diol in free form or in a pharmaceutically acceptable salt form (referred to hereinafter as Compound A), e.g. the hydrochloride, as shown:

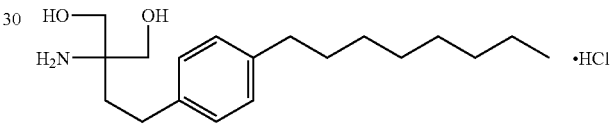

A preferred compound of formula II is the one wherein each of $R'_2$ to $R'_6$ is H and m is 4, i.e. 2-amino-2-{2-[(1-oxo-5-phenylpentyl)phenyl]ethyl}propane-1,3-diol, in free form or in pharmaceutically acceptable salt form (referred to hereinafter as Compound B), e.g the hydrochloride.

A preferred compound of formula III is the one wherein W is $CH_3$, each of $R''_1$ to $R''_3$ is H, $Z_2$ is ethylene, X is heptyloxy and Y is H, i.e. 2-amino-4-(4-heptyloxyphenyl)-2-methylbutanol, in free form or in pharmaceutically acceptable salt form (referred to hereinafter as Compound C), e.g. the hydrochloride. The R-enantiomer is particularly preferred.

A preferred compound of formula IVa is the FTY720-phosphate ($R_{2a}$ is H, $R_{3a}$ is OH, $X_a$ is O, $R_{1a}$ and $R_{1b}$ are OH). A preferred compound of formula IVb is the Compound C-phosphate ($R_{2a}$ is H, $R_{3b}$ is OH, $X_a$ is O, $R_{1a}$ and $R_{1b}$ are OH, $Y_a$ is O and $R_{4a}$ is heptyl). A preferred compound of formula V is Compound B-phosphate.

A preferred compound of formula V is phosphoric acid mono-[(R)-2-amino-2-methyl-4-(4-pentyloxy-phenyl)-butyl]ester.

A preferred compound of formula VIII is (2)-R-2-amino-4-[3-(4-cyclohexyloxybutyl)benzo[b]thien-6-yl]-2-methylbutan-1-ol.

When the compounds of formulae I to XIII have one or more asymmetric centers in the molecule, the various optical isomers, as well as racemates, diastereoisomers and mixtures thereof are embraced.

Examples of pharmaceutically acceptable salts of the compounds of formulae I to XIII include salts with inorganic acids, such as hydrochloride, hydrobromide and sulfate, salts with organic acids, such as acetate, fumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. The compounds and salts of the present invention encompass hydrate and solvate forms.

Binding to S1P receptors can be determined according to the following assays.

A. Binding Affinity of S1P Receptor Agonists to Individual Human S1P Receptors

Transient Transfection of Human S1P Receptors into HEK293 Cells

S1P receptors and $G_i$ proteins are cloned, and equal amounts of 4 cDNAs for the EDG receptor, $G_i$-α, $G_i$-β and $G_i$-γ are mixed and used to transfect monolayers of HEK293 cells using the calcium phosphate precipitate method (M. Wigler et al., Cell. 1977; 11; 223 and DS. Im et al., Mol. Pharmacol. 2000; 57; 753). Briefly, a DNA mixture containing 25 μg of DNA and 0.25 M $CaCl_2$ is added to HEPES-buffered 2 mM $Na_2HPO_4$. Subconfluent monolayers of HEK293 cells are poisoned with 25 mM chloroquine, and the DNA precipitate is then applied to the cells. After 4 h, the monolayers are washed with phosphate-buffered saline and refed media (90% 1:1 Dulbecco's modified essential media (DMEM):F-12+10% fetal bovine serum). The cells are harvested 4872 h after addition of the DNA by scraping in HME buffer (in mM: 20 HEPES, 5 $MgCl_2$, 1 EDTA, pH 7.4) containing 10% sucrose on ice, and disrupted using a Dounce homogenizer. After centrifugation at 800×g, the supernatant is diluted with HME without sucrose and centrifuged at 100,000×g for 1 h. The resulting pellet is rehomogenized and centrifuged a second hour at 100,000×g. This crude membrane pellet is resuspended in HME with sucrose, aliquoted, and snap-frozen by immersion in liquid nitrogen. The membranes are stored at 70° C. Protein concentration is determined spectroscopically by Bradford protein assay.

GTPγS Binding Assay Using S1P Receptor/HEK293 Membrane Preparations

GTPγS binding experiments are performed as described by DS. Im et al., Mol. Pharmacol. 2000; 57:753. Ligand-mediated GTPγS binding to G-proteins is measured in GTP binding buffer (in mM: 50 HEPES, 100 NaCl, 10 $MgCl_2$, pH 7.5) using 25 μg of a membrane preparation from transiently transfected HEK293 cells. Ligand is added to membranes in the presence of 10 μM GDP and 0.1 nM [$^{35}$S]GTPγS (1200 Ci/mmol) and incubated at 30° C. for 30 min. Bound GTPγS is separated from unbound using the Brandel harvester (Gaithersburg, Md.) and counted with a liquid scintillation counter.

The composition of the invention preferably contains 0.01 to 20% by weight of S1P receptor agonists, more preferably 0.1 to 10%, e.g. 0.5 to 5% by weight, based on the total weight of the composition.

The sugar alcohol may act as a diluent, carrier, filler or bulking agent, and may suitably be mannitol, maltitol, inositol, xylitol or lactitol, preferably a substantially non-hygroscopic sugar alcohol, e.g. mannitol (D-mannitol). A single sugar alcohol may be used, or a mixture of two or more sugar alcohols, e.g a mixture of mannitol and xylitol, e.g. in a ratio of 1:1 to 4:1.

In a particularly preferred embodiment, the sugar alcohol is prepared from a spray-dried composition, e.g. mannitol composition, having a high specific surface area. The use of this type of mannitol composition may assist in promoting uniform distribution of the S1P receptor agonist throughout the mannitol in the composition. A higher surface area may be achieved by providing a sugar alcohol, e.g. mannitol, preparation consisting of particles having a smaller mean size and/or a rougher surface on each particle. The use of a spray-dried sugar alcohol, e.g. mannitol, e.g. with a mean particle size of 300 μm or less, has also been found to improve compressibility and hardness of tablets formed from the composition.

Preferably the single point surface area of the sugar alcohol preparation, e.g. mannitol, is 1 to 7 $m^2$/g, e.g. 2 to 6 $m^2$/g or 3 to 5 $m^2$/g. The mannitol preparation may suitably have a mean particle size of 100 to 300 μm, e.g. 150 to 250 μm and a bulk density of 0.4 to 0.6 g/mL, e.g. 0.45 to 0.55 g/mL. A suitable high surface area mannitol is Parteck M200, available commercially from E. Merck.

The composition preferably contains 75 to 99.99% by weight of the sugar alcohol, more preferably 85 to 99.9%, e.g 90 to 99.5% by weight, based on the total weight of the composition.

The composition preferably further comprises a lubricant. Suitable lubricants include stearic acid, magnesium stearate, calcium stearate, zinc stearate, glyceryl palmitostearate, sodium stearyl fumarate, canola oil, hydrogenated vegetable oil such as hydrogenated castor oil (e.g. Cutina® or Lubriwax® 101), mineral oil, sodium lauryl sulfate, magnesium oxide, colloidal silicon dioxide, silicone fluid, polyethylene glycol, polyvinyl alcohol, sodium benzoate, talc, poloxamer, or a mixture of any of the above. Preferably the lubricant comprises magnesium stearate, hydrogenated castor oil or mineral oil. Colloidal silicon dioxide and polyethylene glycol are less preferred as the lubricants.

The composition preferably contains 0.01 to 5% by weight of the lubricant, more preferably 1 to 3% by weight, e.g. about 2% by weight, based on the total weight of the composition.

The composition may comprise one or more further excipients such as carriers, binders or diluents. In particular, the composition may comprise microcrystalline cellulose (e.g. Avicel®), mathylcellulose, hydroxypropylcellulose, hydroxypropylmethylcellulose, starch (e.g. corn starch) or dicalcium phosphate, preferably in an amount of from 0.1 to 90% by weight, e.g. 1 to 30% by weight, based on the total weight of the composition. Where a binder, e.g. microcrystalline cellulose, mathylcellulose, hydroxypropyl cellulose, hydroxypropylmethyl cellulose is used, it is preferably included in an amount of 1 to 8%, e.g. 3 to 6% by weight, based on the total weight of the composition. The use of a binder increases the granule strength of the formulation, which is particularly important for fine granulations. Microcrystalline cellulose and mathylcellulose are particularly preferred where a high tablet hardness and/or longer disintegration time is required. Hydroxypropyl cellulose is preferred where faster disintegration is required. Where appropriate, xylitol may also be added as an additional binder, for example in addition to microcrystalline cellulose, e.g. in an amount up to 20% by weight of the sugar alcohol, e.g. xylitol.

In one embodiment, the composition further comprises a stabiliser, preferably glycine HCl or sodium bicarbonate. The stabiliser may be present in an amount of e.g. 0.1 to 30%, preferably 1 to 20% by weight.

The composition may be in the form of a powder, granule or pallets or a unit dosage form, for example as a tablet or capsule. The compositions of the present invention are well-adapted for encapsulation into an orally administrable capsule shelf, particularly a hard gelatin shell.

Alternatively the compositions may be compacted into tablets. The tablets may optionally be coated, for instance with talc or a polysaccharide (e.g. cellulose) or hydroxypropylmethylcellulose coating.

Where the pharmaceutical capsule is in unit dosage form, each unit dosage will suitably contain 0.5 to 10 mg of the S1P receptor agonist.

The compositions of the invention may show good stability characteristics as indicated by standard stability trials, for example having a shelf life stability of up to one, two or three years, and even longer. Stability characteristics may be determined, e.g. by measuring decomposition products by HPLC analysis after storage for particular times, at particular temperatures, e.g. 20°, 40° or 60° C.

The pharmaceutical compositions of the present invention may be produced by standard processes, for instance by conventional mixing, granulating, sugar-coating, dissolving or lyophilizing processes. Procedures which may be used are known in the art, e.g. those described in L. Lachman et al. The Theory and Practice of Industrial Pharmacy, 3rd Ed, 1986, H. Sucker et al, Pharmazeutische Technologie, Thieme, 1991, Hagers Handbuch der pharmazeutischen Praxis, 4th Ed. (Springer Verlag, 1971) and Remington's Pharmaceutical Sciences, 13th Ed., (Mack Publ., Co., 1970) or later editions.

In one aspect, the present invention relates to a process for producing a pharmaceutical composition, comprising:
(a) mixing an S1P receptor agonist with a sugar alcohol;
(b) milling and/or granulating the mixture obtained in (a); and
(c) mixing the milled and/or granulated mixture obtained in (b) with a lubricant.

By using this process, a preparation having a good level of content and blend uniformity (i.e. a substantially uniform distribution of the S1P receptor agonist throughout the composition), dissolution time and stability is obtained.

The S1P receptor agonist, e.g. 2-amino-2-[2-(4-octylphenyl)ethyl]propane-1,3diol, hydrochloride, may optionally be micronized, and/or pre-screened, e.g. with a 400 to 500 μm mesh screen, before step (a) in order to remove lumps. The mixing step (a) may suitably comprise blending the S1P receptor agonist and the sugar alcohol, e.g. mannitol in any suitable blender or mixer for e.g. 100 to 400 revolutions.

The process may be carried out by dry mixing the components. In this embodiment the milling step (b) may suitably comprise passing the mixture obtained in (a) through a screen, which preferably has a mesh size of 400 to 500 μm. Process step (a) may comprise the step of mixing the total amount of S1P receptor agonist at first with a low amount of sugar alcohol, e.g. from 5 to 25% by weight of the total weight of sugar alcohol, in order to form a pre-mix. Subsequently the remaining amount of sugar alcohol is added to the pre-mix. Step (a) may also comprise the step of adding a binder solution, e.g. methylcellulose and/or xylitol, e.g. an aqueous solution, to the mixture. Alternatively the binder is added to the mix dry and water is added in the granulation step.

The milled mixture obtained in (b) may optionally be blended once more before mixing with the lubricant. The lubricant, e.g. magnesium stearate, is preferably pre-screened, e.g. with a 800 to 900 μm screen, before mixing.

Alternatively, a wet granulation process is employed. In this embodiment, the S1P receptor agonist is preferably first dry-mixed with the desired sugar alcohol, e.g. mannitol, and the obtained sugar alcohol/S1P receptor agonist mixture is then dry-mixed with a binder such as hydroxypropyl cellulose or hydroxypropylmethyl cellulose. Water is then added and the mixture granulated, e.g. using an automated granulator. The granulation is then dried and milled.

If desirable, an additional amount of binder may be added in step (c) to the mixture obtained in (b).

The process may comprise a further step of tabletting or encapsulating the mixture obtained in (c), e.g. into a hard gelatin capsule using an automated encapsulation device. The capsules may be coloured or marked so as to impart an individual appearance and to make them instantly recognizable. The use of dyes can serve to enhance the appearance as well as to identify the capsules. Dyes suitable for use in pharmacy typically include carotinoids, iron oxides, and chlorophyll. Preferably, the capsules of the invention are marked using a code.

The pharmaceutical compositions of the present invention are useful, either alone or in combination with other active agents, for the treatment and prevention of conditions e.g. as disclosed in U.S. Pat. No. 5,604,229, WO 97/24112, WO 01/01978, U.S. Pat. No. 6,004,565, U.S. Pat. No. 6,274,629 and JP-14316985, the contents of which are incorporated herein by reference.

In particular, the pharmaceutical compositions are useful for:

a) treatment and prevention of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation; particularly in the treatment of acute or chronic allo- and xenograft rejection or in the transplantation of insulin producing cells, e.g. pancreatic islet cells;

b) treatment and prevention of autoimmune disease or of inflammatory conditions, e.g. multiple sclerosis, arthritis (for example rheumatoid arthritis), inflammatory bowel disease, hepatitis, etc.;

c) treatment and prevention of viral myocarditis and viral diseases caused by viral mycocarditis, including hepatitis and AIDS.

Accordingly, in further aspects the present invention provides:

1. A composition as defined above, for use in treating or preventing a disease or condition as defined above.

2. A method of treating a subject in need of immunomodulation, comprising administering to the subject an effective amount of a composition as defined above.

3. A method of treating or preventing a disease or condition as defined above, comprising administering to the subject a composition as defined above.

4. Use of a pharmaceutical composition as defined above for the preparation of a medicament for the prevention or treatment of a disease or condition as defined above.

The invention will now be described with reference to the following specific embodiments.

EXAMPLE 1

Micronized Compound A, e.g. 2-amino-2-[2-(4-octylphenyl)ethyl]propan e-1,3-diol, hydrochloride salt (FTY720), is screened and 116.7 g of the screened compound is mixed with 9683.3 g mannitol (Parteck M200 from E. Merck). The mixture is then milled in a Frewitt MGI device (Key International inc. USA) using a 30 mesh screen. Magnesium stearate is screened using a 20 mesh screen and 200 g of the screened compound blended with the FTY720/mannitol mixture to produce a product composition.

The product composition is then compacted on a tablet press using a 7 mm die to form 120 mg tablets, each containing:

| | |
|---|---:|
| Compound A, e.g. FTY720* | 1.4 mg |
| Mannitol M200 | 116.2 mg |
| Magnesium stearate | 2.4 mg |
| Total | 120 mg |

*1 mg of Compound A in free form is equivalent to 1.12 mg of FTY720.

EXAMPLE 2

In a further example, the process of example 1 is repeated except that the magnesium stearate is replaced by Cutina® (hydrogenated castor oil).

EXAMPLE 3

Compound A, e.g. FTY720, and mannitol (Parteck MA200 from E. Merck) are each screened separately using an 18 mesh screen. 1.9 g screened FTY720 is mixed with 40 g screened mannitol for 120 revolutions in a blender at 32 rpm. The FTY720/mannitol mixture is then screened through a 35 mesh screen.

The screened FTY20/mannitol mixture is added to a granulator along with a further 340.1 g mannitol and 12 g hydroxypropylcellulose. The mixture is mixed for 3 minutes. Water is then added at a rate of 100 ml/minute and the mixture granulated for 2 minutes. The granulation is transferred into a tray dryer and dried at 50° C. for 150 minutes.

The mixture is then milled in a Frewitt MGI device using a 35 mesh screen. Magnesium stearate is screened and 6 g of the screened compound is blended for 90 revolutions at 32 rpm with the FTY720/mannitol mixture to produce a product composition showing a substantially uniform distribution of the S1P receptor agonist throughout the mannitol in the blend.

The product composition is then filled into size 3 hard gelatin shells on an Hoflinger & Karg 400 encapsulation device. 120 mg of the product composition is added to each capsule. Therefore each capsule contains:

| | |
|---|---:|
| FTY720* | 0.56 mg |
| Mannitol M200 | 114.04 mg |
| Hydroxypropylcellulose | 3.6 mg |
| Magnesium stearate | 1.8 mg |
| Total | 120 mg |

EXAMPLE 4

In a further example, the process of example 3 is repeated except that the magnesium stearate is replaced by Cutina® (hydrogenated castor oil).

EXAMPLE 5

In a further example, the process of example 3 is repeated except that the hydroxypropyl cellulose is replaced by hydroxypropylmethyl cellulose.

EXAMPLE 6a

Micronized Compound A, erg. FTY720, is screened using a 400 μm (40 mesh) screen. 58.35 g of the screened compound is mixed with 4841.65 g mannitol (Parteck M200 from E. Merck) in a 25 L Bohle bin blender for 240 blending revolutions. The mixture is then milled in a Frewitt MGI device using a 400 μm mesh screen, and the milled mixture is blended once more. Magnesium stearate is screened and 100 g of the screened compound is blended with the FTY720/mannitol mixture to produce a product composition showing a substantially uniform distribution of the S1P receptor agonist throughout the mannitol in the blend.

The product composition is then filled into size 3 hard gelatin shells on an Hoflinger & Karg 400 encapsulation device. 120 mg of the product composition is added to each capsule. Therefore each capsule contains:

| | |
|---|---:|
| FTY720* | 1.4 mg |
| Mannitol M200 | 116.2 mg |
| Magnesium stearate | 2.4 mg |
| Total | 120 mg |

EXAMPLE 6b

In an alternative embodiment, capsules are manufactured using the components and in the amounts as described in Example 6a, but the FTY720 is first mixed with 14 mg mannitol (before screening). This mixture is then screened as described above. The screened mixture is then blended with the remaining mannitol and the magnesium stearate is added, followed by additional blending and filling into capsules.

EXAMPLES 7 AND 8 in further examples, capsules are prepared as described in example 6, except that each capsule contains each component in the following amounts:

| | Example 7 | Example 8 |
|---|---:|---:|
| FTY720* | 2.8 mg | 5.6 mg |
| Mannitol M200 | 114.8 mg | 112 mg |
| Magnesium stearate | 2.4 mg | 2.4 mg |
| Total | 120 mg | 120 mg |

EXAMPLES 9 TO 11

In further examples, capsules are prepared as described in examples 6 to 8, except that the magnesium stearate is replaced in each case by Cutina® (hydrogenated castor oil).

EXAMPLES 12 TO 22

In further examples, capsules or tablets are prepared as described in examples 1 to 11, except that FTY720 is replaced in each case by 2-amino-2-{2-[4-(1-oxo-5-phenylpentyl) phenyl]ethyl}propane-1,3-diol hydrochloride.

EXAMPLES 23 AND 24

Capsules containing the following ingredients are prepared, by weighing each component and mixing in a mortar, then filling into capsules:

|  | Example 23 | Example 24 |
|---|---|---|
| FTY720 | 5 mg | 1 mg |
| D-mannitol | 83.7 mg | 117 mg |
| Corn starch | 24 mg | — |
| Avicel ® PH101 | 12 mg | — |
| Hydroxypropylcellulose | 0.3 mg | 7 mg |
| Talc | 3 mg | 3 mg |
| Lubri wax ® 101 | 2 mg | 2 mg |
| Total | 130 mg | 130 mg |

EXAMPLES 25 TO 27

Pharmaceutical compositions containing the following ingredients are produced:

|  | Example 25 | Example 26 | Example 27 |
|---|---|---|---|
| FTY720 | 5 g | 10 g | 100 g |
| D-mannitol | 991 g | 986 g | 897 g |
| Methylcellulose SM-25 | 4 g | 4 g | 3 g |
| Total | 1000 g | 1000 g | 1000 g |

The FTY720 and a proportion of the D-mannitol equal to twice the weight of the FTY720 are mixed in a Microspeed Mixer MS-E type (Palmer, USA) for 2 minutes at 1200 rpm. The remaining D-mannitol is added to the mixture and mixed for another 2 minutes. 80 or 60 milliliters of 5% methylcellulose SM-25 solution is supplied from a hopper and granulated under the same conditions. The mixture is extruded through a screen with 0.4 mm apertures using an extruder RG-5 type. The extruded material is dried at 65° C. by a fluidized-bed granulator STREA I Type (Patheon, Canada) and then sieved through a 24 mesh sieve. Fine particles which pass through a 60 mesh sieve are removed. The obtained fire granules are filled into capsules by a Zuma capsule-filling machine (100 mg per capsule).

EXAMPLES 28 TO 31

Tablets containing the following ingredients (in mg) are produced:

|  | Example 28 | Example 29 | Example 30 | Example 31 |
|---|---|---|---|---|
| FTY720 | 1 | 1 | 1 | 1 |
| D-mannitol | 62.3 | 62.3 | 62.0 | 62.0 |
| Xylitol* | 26.7(5.4) | 26.7(5.4) | 26.6 | 26.6 |
| Methylcellulose | — | — | 0.4 | 0.4 |
| Microcrystalline cellulose | 24.0 | — | 24.0 | — |
| Low-substituted Hydroxypropyl-cellulose | — | 24.0 | — | 24.0 |
| Hydrogenated oil | 6.0 | 6.0 | 6.0 | 6.0 |
| Total | 120.0 | 120.0 | 120.0 | 120.0 |

*The amount of xylitol indicated in brackets was used as a binder.

FTY720, D-mannitol and xyiitol are placed in a fluid-bed granulator (MP-01 model, Powrex), mixed for five minutes, and granulated under spray of binder solution, followed by drying till the exhaust temperature reaches 40° C. The granulation conditions are as shown below. Dried powder is passed through a 24-mesh sieve, added to the specified amount of filler and lubricant, and mixed in a mixer (Tubular Mixer, WAB) for three minutes to make the powder for compression.

The resulting powder is compressed by a tabletting machine (Cleanpress correct 12 HUK, Kikushui Seisakusho) with a punch of 7 mm i.d.×7.5 mm R at a compression force of 9800 N.

Granulation Conditions:

| Item | Setting |
|---|---|
| Charge-in amount | 1170 g |
| Volume of intake-air | 50 m³/min |
| Temperature of intake-air | 75° C. |
| Flow rate of spray solution | 15 mL/min |
| Spray air pressure | 15 N/cm² |
| Spray air volume | 30 L/min |
| Volume of binder solution | 351 mL |

EXAMPLES 32 TO 39

Tablets containing the following ingredients (in mg) are produced:

|  | Ex. 32 | Ex. 33 | Ex. 34 | Ex. 35 | Ex. 36 | Ex. 37 | Ex. 38 | Ex. 39 |
|---|---|---|---|---|---|---|---|---|
| FTY720 | 1 | 1 | 1 | 1 | 1 | 1 | 1 | 1 |
| D-mannitol | 116.6 | 114.2 | 104.6 | 114.2 | 104.6 | 116.6 | 115.4 | 113 |
| magnesium stearate | 2.4 | 2.4 | 2.4 | 2.4 | 2.4 | — | — | — |
| glycine HCl | — | 2.4 | 12 | — | — | — | — | — |
| sodium bicarbonate | — | — | — | 2.4 | 12 | — | — | — |
| zinc stearate | — | — | — | — | — | 2.4 | — | — |
| silicone fluid | — | — | — | — | — | — | 3.6 | — |
| mineral oil | — | — | — | — | — | — | — | 6 |
| Total | 120.0 | 120.0 | 120.0 | 120.0 | 120.0 | 120.0 | 120.0 | 120.0 |

The invention claimed is:

1. A solid pharmaceutical composition suitable for oral administration, comprising:
   (a) a S1P receptor agonist which is selected from 2-amino-2-[4-(3-benzyloxyphenoxy)-2-chlorophenyl]propyl-1,3-propane-diol or 2-amino-2-[4-(3-benzyloxyphenylthio)-2-chlorophenyl]propyl-1,3-propane-diol, 2-amino-2-[4-(3-benzyloxyphenylthio)-2-chlorophenyl]-2-ethyl-1,3-propane-diol, and its phosphates or a pharmaceutically acceptable salt thereof; and
   (b) a sugar alcohol.

2. The composition of claim 1, wherein the salt is the hydrochloride.

3. A composition according to claim 1, wherein the sugar alcohol is a non-hygroscopic sugar alcohol or a mixture thereof.

4. A composition according to claim 1, wherein the sugar alcohol comprises mannitol.

5. A composition according to claim 1, further comprising a lubricant.

6. A composition according to claim 5, wherein the lubricant comprises magnesium stearate.

7. A composition according to claim 1, comprising 0.01 to 20% by weight of the S1P receptor agonist.

8. A composition according to claim 7, comprising 0.5 to 5% by weight of the S1P receptor agonist.

9. A composition according to claim 1, comprising 75 to 99.99% by weight of the sugar alcohol.

10. A composition according to claim 9, comprising 90 to 99.5% by weight of the sugar alcohol.

11. A composition according to claim 5, comprising 0.01 to 5% by weight of the lubricant.

12. A composition according to claim 11, comprising 1.5 to 2.5% by weight of the lubricant.

13. A composition according to claim 1, wherein the S1P receptor agonist is micronized.

14. A composition according to claim 13, wherein the S1P receptor agonist is pre-screened with a 400 to 500 μm mesh screen.

15. A composition according to claim 1, in the form of a tablet.

16. A composition according to claim 1 in the form of a capsule.

17. A method of treating organ or tissue transplant rejection, graft versus host disease, an autoimmune disease, an inflammatory condition, viral myocarditis or a viral disease caused by viral myocarditis in a subject in need thereof, comprising administering to said subject a pharmaceutical composition according to claim 1.

18. A method according to claim 17, wherein the disease or condition that is treated is multiple sclerosis.

19. A solid pharmaceutical composition suitable for oral administration, comprising mannitol and 2-amino-2-[2-(4-octylphenyl)ethyl]propane-1,3-diol or a pharmaceutically acceptable salt thereof.

20. A composition according to claim 19, further comprising a lubricant.

21. A composition according to claim 20, wherein the lubricant comprises magnesium stearate.

22. A composition according to claim 19, wherein the compound 2-amino-2-[2-(4-octylphenyl)ethyl]propane-1,3-diol, or a pharmaceutically acceptable salt thereof, is present in an amount of 0.5 to 5% by weight, based on the total weight of the composition.

23. A composition according to claim 19, wherein mannitol is present in an amount of 90 to 99.5% by weight, based on the total weight of the composition.

24. A composition according to claim 19, wherein the lubricant is present in an amount of 1.5 to 2.5% by weight, based on the total weight of the composition.

25. A composition according to claim 19, wherein said composition is in the form of a tablet.

26. A composition according to claim 19, wherein said composition is in the form of a capsule.

27. A composition according to claim 19, wherein the mannitol has a mean particle size of 100 to 300 μm.

28. A composition according to claim 27, wherein the mannitol has a mean particle size of 150 to 250 μm.

29. A composition according to claim 19, wherein the mannitol has a bulk density of 0.4 to 0.6 g/mL.

30. A composition according to claim 29, wherein the mannitol has a bulk density of 0.45 to 0.55 g/mL.

31. A composition according to claim 19, wherein the mannitol has a single point surface area of 1 $m^2/g$ to 7 $m^2/g$.

32. A pharmaceutical composition according to claim 1, wherein the S1P receptor agonist is 2-amino-2-[2-(4-octylphenyl)ethyl]propane-1,3-diol or a pharmaceutically acceptable salt thereof.

* * * * *

UNITED STATES PATENT AND TRADEMARK OFFICE
CERTIFICATE OF CORRECTION

PATENT NO. : 8,324,283 B2
APPLICATION NO. : 12/189323
DATED : December 4, 2012
INVENTOR(S) : Tomoyuki Oomura et al.

It is certified that error appears in the above-identified patent and that said Letters Patent is hereby corrected as shown below:

Column 17, line 2 Claim 1, replace:

"1. A solid pharmaceutical composition suitable for oral administration, comprising:

(a)  a S1P receptor agonist which is selected from 2-amino-2-[4-(3-benzyloxyphenoxy)-2-chlorophenyl]propyl-1,3-propane-diol or 2-amino-2-[4-(3-benzyloxyphenylthio)-2- chlorophenyl]propyl-1,3-propane-diol, 2-amino-2-[4-(3-benzyloxyphenylthio)-2- chlorophenyl]-2-ethyl-1,3-propane-diol, and its phosphates or a pharmaceutically acceptable salt thereof; and (b)  a sugar alcohol."

with

--1. A solid pharmaceutical composition suitable for oral administration, comprising:

(a)  a S1P receptor agonist which is selected from 2-amino-2-[2-(4-octylphenyl)ethyl]propane-1,3-diol, 2-amino-2-[4-(3-benzyloxyphenoxy)-2-chlorophenyl]propyl-1,3-propane-diol, 2-amino-2-[4-(3-benzyloxyphenylthio)-2-chlorophenyl]propyl-1,3-propane-diol, or 2-amino-2-[4-(3-benzyloxyphenylthio)-2-chlorophenyl]-2-ethyl-1,3-propane-diol, and its phosphates or a pharmaceutically acceptable salt thereof; and (b)  a sugar alcohol.--

Signed and Sealed this
Twelfth Day of March, 2013

Teresa Stanek Rea
*Acting Director of the United States Patent and Trademark Office*